(12) United States Patent
Pavesi et al.

(10) Patent No.: US 10,711,234 B2
(45) Date of Patent: Jul. 14, 2020

(54) MICROFLUIDIC PLATFORM FOR INVESTIGATING CELL-BASED INTERACTIONS

(71) Applicant: AIM BIOTECH PTE. LTD., Singapore (SG)

(72) Inventors: Andrea Pavesi, Singapore (SG); Sei Hien Lim, Singapore (SG); Swee Khuan Lim, Singapore (SG); Chee Mun Kuan, Singapore (SG)

(73) Assignee: AIM BIOTECH PTE. LTD., Singapore (SG)

( * ) Notice: Subject to any disclaimer, the term of this patent is extended or adjusted under 35 U.S.C. 154(b) by 185 days.

(21) Appl. No.: 15/525,937

(22) PCT Filed: Nov. 9, 2015

(86) PCT No.: PCT/SG2015/050441
§ 371 (c)(1),
(2) Date: May 10, 2017

(87) PCT Pub. No.: WO2016/076795
PCT Pub. Date: May 19, 2016

(65) Prior Publication Data
US 2018/0327700 A1 Nov. 15, 2018

Related U.S. Application Data

(60) Provisional application No. 62/077,942, filed on Nov. 11, 2014.

(51) Int. Cl.
*C12M 3/06* (2006.01)
*C12M 1/32* (2006.01)
(Continued)

(52) U.S. Cl.
CPC ....... *C12M 23/16* (2013.01); *B01L 3/502761* (2013.01); *C12M 23/12* (2013.01);
(Continued)

(58) Field of Classification Search
CPC ...... C12M 23/16; C12M 23/24; C12M 23/40; C12M 23/22; C12M 23/12;
(Continued)

(56) References Cited

U.S. PATENT DOCUMENTS

| 2002/0110496 A1* | 8/2002 | Samsoondar | B01L 3/508 |
| | | | 422/560 |
| 2002/0114739 A1* | 8/2002 | Weigl | A61B 5/0031 |
| | | | 422/400 |

(Continued)

FOREIGN PATENT DOCUMENTS

| WO | WO 1998/055852 A1 | 12/1998 |
| WO | WO 2009/126524 A2 | 10/2009 |
| WO | WO 2010/056755 A2 | 5/2010 |

OTHER PUBLICATIONS

Berthier, E., et al., Engineers are from PDMS-land, Biologists are from Polystyrenia, Lab on a Chip, vol. 12, pp. 1224-1237, 2012.
(Continued)

*Primary Examiner* — Michael L Hobbs
(74) *Attorney, Agent, or Firm* — Knobbe, Martens, Olson & Bear, LLP

(57) ABSTRACT

A microfluidic platform for investigating cell-based interactions with a chip base is made of a suitable plastics material with the appropriate optical properties. The chip base has a plurality of ports in fluid communication with a microfluidic channel for containing a culture medium in which cells are held. A gas permeable laminate is bonded to a bottom surface of the chip base. Each port has an internal inlet, connecting the port with the microfluidic channel, and a
(Continued)

trough for containing a small reservoir of culture medium fluid adjacent to the inlet. When in use, culture medium can be aspirated from the microfluidic channel via the trough rather than directly via the internal inlet.

32 Claims, 5 Drawing Sheets

(51) Int. Cl.
  *C12M 1/00* (2006.01)
  *B01L 3/00* (2006.01)
  *C12M 1/04* (2006.01)
(52) U.S. Cl.
  CPC ............ *C12M 23/22* (2013.01); *C12M 23/24* (2013.01); *C12M 23/40* (2013.01); *B01L 2200/025* (2013.01); *B01L 2200/0684* (2013.01); *B01L 2300/0809* (2013.01); *B01L 2300/0874* (2013.01); *B01L 2300/12* (2013.01)
(58) Field of Classification Search
  CPC ....... B01L 3/502761; B01L 2200/0684; B01L 2200/025; B01L 2300/0874; B01L 2300/0809; B01L 2300/12
  See application file for complete search history.

(56) References Cited

U.S. PATENT DOCUMENTS

| | | |
|---|---|---|
| 2005/0266582 A1 | 12/2005 | Modlin et al. |
| 2007/0116600 A1* | 5/2007 | Kochar .................. G01N 21/76 422/65 |
| 2007/0264705 A1* | 11/2007 | Dodgson .............. A61B 17/435 435/283.1 |
| 2010/0056394 A1 | 3/2010 | Chang et al. |
| 2011/0011781 A1* | 1/2011 | Blankenstein .... B01L 3/502715 210/205 |

OTHER PUBLICATIONS

Mair, D.A., et al., Injection molded microfluidic chips featuring integrated Interconnects, Lab on a Chip, vol. 6, pp. 1346-1354, 2006.

International Search Report, dated Feb. 26, 2016, in International Application No. PCT/SG2015/050441.

Written Opinion, dated Feb. 26, 2016, in International Application No. PCT/SG2015/050441.

* cited by examiner

MICROFLUIDIC PLATFORM FOR INVESTIGATING CELL-BASED INTERACTIONS

PRIORITY AND CROSS-REFERENCE TO RELATED APPLICATIONS

This application is the U.S. National Phase Application under 35 U.S.C. § 371 of International Application No. PCT/SG2015/050441, filed Nov. 9, 2015, designating the U.S. and published as WO 2016/076795 A1 on May 19, 2016, which claims the benefit of U.S. Provisional Application No. 62/077,942, filed Nov. 11, 2014. Any and all applications for which a foreign or a domestic priority is claimed is/are identified in the Application Data Sheet filed herewith and is/are hereby incorporated by reference in their entirety under 37 C.F.R. § 1.57.

FIELD OF THE INVENTION

The present invention relates to microfluidic technologies used to culture cells in a three-dimensional (3D) microenvironment and relates more specifically, although not exclusively, to a microfluidic plastic device.

BACKGROUND TO THE INVENTION

Microfluidic technologies enable users to culture cells in a more physiological three-dimensional (3D) microenvironment, offering the capabilities of high-resolution real-time imaging, multiple communicating cells types and control over flow and gradients. International Patent Application No PCT/US2009/039434 describes Three-Dimensional Microfluidic Platforms and Methods of Use Thereof. The material used to make these prior art devices is polydimethylsiloxane (PDMS), a moldable silicone that is optically clear and gas permeable. PDMS is commonly used for rapid prototyping with soft lithography processes to produce microfluidic devices. However, PDMS is not an ideal material for cell-based applications for reasons outlined in detail by Beebe et al. in Lab Chip, 2012, 12, 1224-1237. In brief, some of the disadvantages include:
- PDMS is a permeable material prone to the bulk absorption of hydrophobic compounds—Biological assays investigating hydrophobic drugs/proteins will be affected, as their effective concentration would be lowered by bulk absorption.
- PDMS is prone to evaporation—The water vapour permeability of PDMS is a disadvantage in microfluidic devices where the volume of culture media used is small. Evaporation may cause osmolarity shifts and affect cell behaviour.
- PDMS will recover its hydrophobicity—PDMS is normally hydrophobic and is treated with plasma to increase the hydrophilicity of the surface. A hydrophilic surface facilitates specific processes in microfluidics, such as surface functionalization and microchannel filling. However, plasma-treated PDMS surfaces recover their hydrophobicity due to the diffusion of polymer chains from the bulk to the surface. Users then have to repeat plasma treatment prior to use; besides the inconvenience, many users may not have access to plasma chambers.
- PDMS is unsuitable for high volume manufacturing—The manufacturing cycle time for PDMS is unacceptably long due to its lengthy curing and processing time.

The present invention was developed with a view to providing a three dimensional microfluidic platform made of plastics material that is less susceptible to the problems of the prior art devices made of PDMS. The microfluidic platform of the present invention may also incorporate a number of other advantageous features that improve its functionality.

References to prior art documents in this specification are provided for illustrative purposes only and are not to be taken as an admission that such prior art is part of the common general knowledge in Singapore or elsewhere.

SUMMARY OF THE INVENTION

According to one aspect of the present invention there is provided a microfluidic platform for investigating cell-based interactions, the platform comprising:
a chip base made of a suitable plastics material with the appropriate optical properties, the chip base having a plurality of ports in fluid communication with a microfluidic channel for containing a culture medium in which cells are held.

Preferably the chip base is made from an engineering plastics material that can be injection molded and is optically clear. Typically the plastics material is selected from the group consisting of: polycarbonates (PC), polystyrenes (PS), polyethylenes (PE), cyclic olefin co-polymers (COC), cyclic olefin polymers (COP).

Preferably the platform further comprises a gas permeable laminate bonded to a bottom surface of the chip base.

Preferably the gas permeable laminate is made from a polymer with low bulk density. Typically the polymer of low bulk density is selected from the group consisting of: polymethylpentene (PMP) and poly(1-trimethylsilyl-1-propyne) (PTMSP), or from polymethylated polymers such as polymethylated poly(diphenylacetylene), or from polymers that achieve sufficient gas permeability through other means. Typically the laminate is bonded to the chip base by heat lamination, solvent bonding, adhesion (with wet or dry adhesives), or by other means depending on the specific materials used for the chip base and laminate respectively. Preferably the gas permeable laminate is optically clear.

Typically the chip base has a plurality of microfluidic channels of elongate configuration arranged in a linear array, each microfluidic channel being substantially parallel to an adjacent channel. Preferably each microfluidic channel has a pair of ports, one port provided at each end respectively. Preferably the ports all open onto an upper surface of the chip base. Preferably the microfluidic channels are arranged into pairs with a third microfluidic channel provided there between, the third channel being arranged so as to permit controlled fluid communication between the pair of microfluidic channels and the third microfluidic channel. Typically the third microfluidic channel is filled with a hydrogel or other extracellular matrix. Preferably all of the microfluidic channels are formed in a bottom surface of the chip base and the gas permeable laminate bonded to the bottom surface of the chip base encloses the channels.

Advantageously the chip base is formed with a plurality of reservoirs molded into the upper surface thereof which are not in fluid communication with the ports, wherein, in use, each reservoir is adapted to hold sterile water, a hydrogel or other substance to create a humid environment around the device.

Typically the chip base is of generally elongate, rectangular configuration, with the ports arranged along its respective longitudinal edges.

According to another aspect of the present invention there is provided a method of manufacturing a microfluidic platform for investigating cell-based interactions, the method comprising the steps of:

molding a chip base from a suitable plastics material with appropriate optical properties, the chip base having a plurality of ports in fluid communication with a microfluidic channel for containing a culture medium in which cells are held.

Preferably the step of molding the chip base involves injection molding using an engineering plastics material that is optically clear. Typically the plastics material is selected from the group consisting of: polycarbonates (PC), polystyrenes (PS), polyethylenes (PE), cyclic olefin co-polymers (COC), and cyclic olefin polymers (COP).

Typically the method further comprises the step of bonding a gas permeable laminate to a bottom surface of the chip base.

Preferably the gas permeable laminate is optically clear and is made from a polymer with low bulk density. Typically the polymer of low bulk density is selected from the group consisting of: polymethylpentene (PMP) and poly(1-trimethylsilyl-1-propyne) (PTMSP), polymethylated polymers such as polymethylated poly(diphenylacetylene), or polymers that achieve sufficient gas permeability through other means.

Typically the step of bonding the laminate to the chip base involves laminating the laminate to the chip base by heat lamination. Alternatively the step of bonding the laminate to the chip base involves solvent bonding, adhesion bonding (with wet or dry adhesives), or other bonding means depending on the specific materials used for the chip base and laminate respectively.

According to a further aspect of the present invention there is provided a microfluidic platform for investigating cell-based interactions, the platform comprising:

a chip base having a plurality of ports in fluid communication with a microfluidic channel for containing a fluid culture medium in which cells are held, each port having an internal inlet, connecting the port with the microfluidic channel, and a trough for containing a small reservoir of the culture medium adjacent to the inlet wherein, in use, culture medium can be aspirated from the microfluidic channel via the trough rather than directly via the internal inlet.

In one embodiment the inlet is provided centrally of the port and the trough is of annular configuration surrounding the inlet.

Typically the bottom of the trough is of semicircular cross-section.

Preferably the ports of the microfluidic platform are designed as modular attachment interfaces.

Advantageously the ports are adapted to receive a universal modular luer connector for attaching standard luer fittings, such as tubing connectors and syringe pumps to the microfluidic platform.

Advantageously a plurality of the microfluidic chips can be received and held in a single microplate holder. Preferably the holder comprises a plurality of internal reservoirs provided in an upper surface thereof, which are not in fluid communication with the chips, wherein, in use, each reservoir is adapted to hold sterile water, a hydrogel or other substance to create a humid environment around the chips.

Throughout the specification, unless the context requires otherwise, the word "comprise" or variations such as "comprises" or "comprising", will be understood to imply the inclusion of a stated integer or group of integers but not the exclusion of any other integer or group of integers. Likewise the word "preferably" or variations such as "preferred", will be understood to imply that a stated integer or group of integers is desirable but not essential to the working of the invention.

BRIEF DESCRIPTION OF THE DRAWINGS

The nature of the invention will be better understood from the following detailed description of several specific embodiments of the microfluidic platform, given by way of example only, with reference to the accompanying drawings, in which.

DETAILED DESCRIPTION OF PREFERRED EMBODIMENTS

Figure 1A:
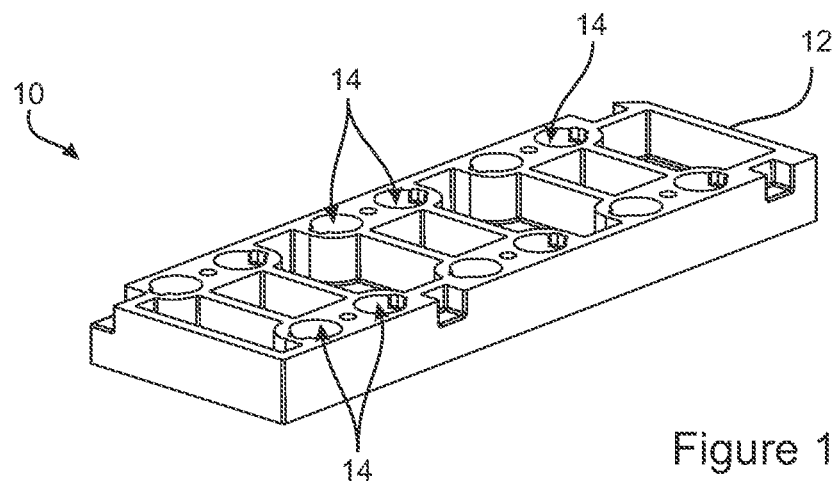
FIG. 1(a) is an isometric view of a first embodiment of a microfluidic platform according to the present invention.
Figure 1B:
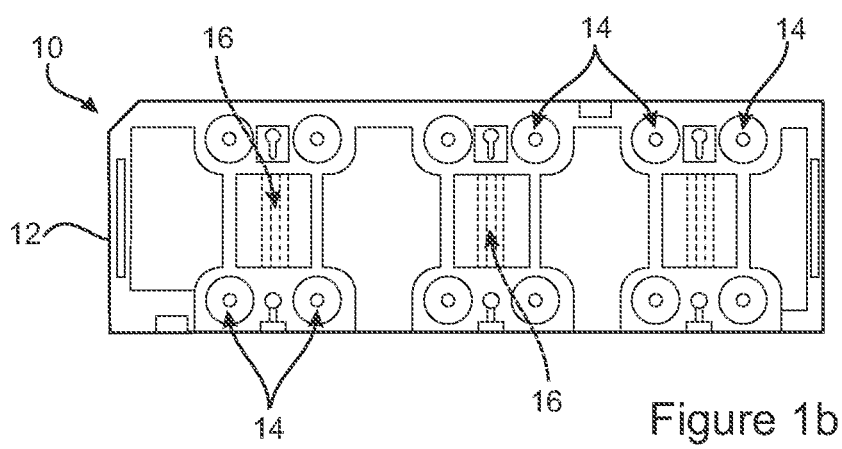
FIG. 1(b) is a plan view of the microfluidic platform of FIG. 1(a)
Figure 2:
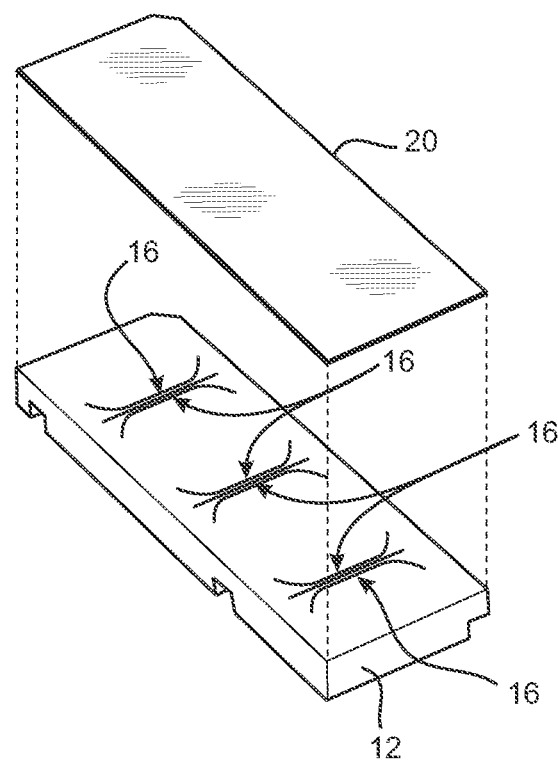
FIG. 2 is a cross-sectional view of the microfluidic platform of FIG. 1 showing a preferred arrangement of the chip base and gas permeable laminate.

A preferred embodiment of a microfluidic platform 10 for investigating cell-based interactions in accordance with the invention, as illustrated in FIGS. 1 and 2, comprises a chip base 12 made of a suitable plastics material with the appropriate optical properties. The chip base 12 has a plurality of ports 14 in fluid communication with a microfluidic channel 16 for containing a culture medium 17 in which cells are held.

Figure 10:
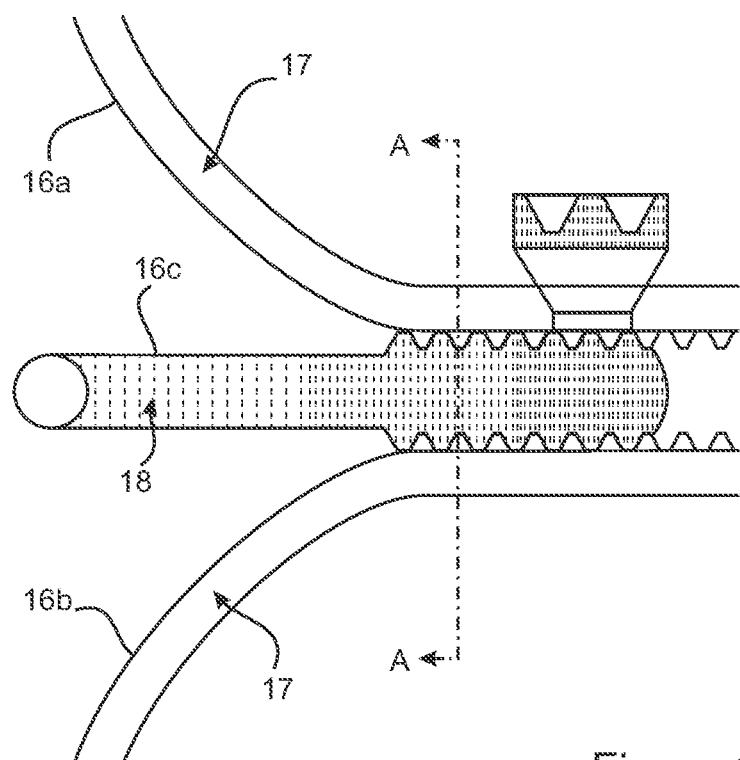
FIG. 10 is an enlarged bottom of a preferred embodiment of the microfluidic channels in the microfluidic platform of FIG. 1; and, FIG. 11 is an enlarged cross-section view of the microfluidic channels through the line A-A in FIG. 10.
Figure 11:
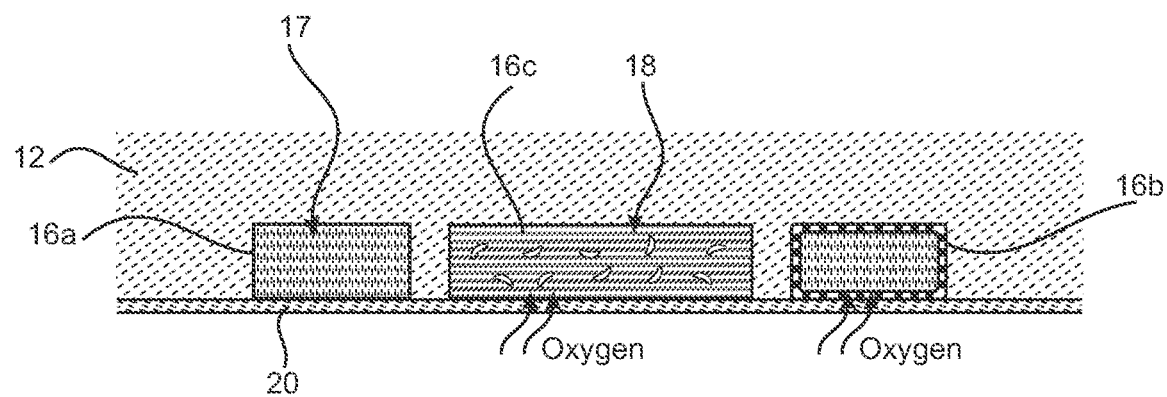

Typically the chip base 12 has a plurality of microfluidic channels 16 of elongate configuration arranged in a linear array, each microfluidic channel 16 being substantially parallel to an adjacent channel, as can be seen most clearly in FIGS. 10 and 11. Each microfluidic channel 16 has first and second ports 14 provided at each end respectively, as can be seen most clearly in FIG. 4. Preferably the ports 14 all open onto an upper surface of the chip base 12. Typically the chip base 12 is of generally elongate, rectangular configuration, with the ports 14 arranged along its respective longitudinal edges. Typical dimensions of the chip base 12 are 75 mm in length, 25 mm in width, and 6 mm in depth. The microfluidic channels 16 are typically 250 microns deep.

Preferably the microfluidic channels 16 are arranged into pairs 16a, 16b with a third microfluidic channel 16c provided there between, as illustrated in FIGS. 10 and 11. The third channel 16c is arranged so as to permit controlled fluid communication between the pair of microfluidic channels 16a, 16b and the third microfluidic channel 16c. Typically the third microfluidic channel 16c is filled with a hydrogel 18 or other extracellular matrix.

Preferably the chip base 12 is made from an engineering plastics material that can be injection molded and is optically clear. Typically the plastics material is selected from the group consisting of (but not limited to): polycarbonates (PC), polystyrenes (PS), polyethylenes (PE), cyclic olefin co-polymers (COC), cyclic olefin polymers (COP).

Plastics such as polycarbonate, polystyrene, etc. have historically been used to make cell culture devices in large scales. Traditional cell culture devices are flasks or wells that have large air head spaces and media volumes, so gas exchange is easily achieved. However, microfluidic devices consist of small volumes in sealed channels, and gas exchange becomes a limiting factor as most plastics are gas impermeable. This limitation may be been overcome by combining the plastic chip base 14 with a gas permeable laminate 20.

Preferably the gas permeable laminate 20 is optically clear and is made from a polymer with low bulk density. Typically the polymer of low bulk density is selected from the group consisting of: polymethylpentene (PMP) and poly(1-trimethylsilyl-1-propyne) (PTMSP), or from polymethylated polymers such as polymethylated poly(diphenylacetylene), or from polymers that achieve sufficient gas permeability through other means. Preferably all of the microfluidic channels 16 are formed in a bottom surface of the chip base 12 and the gas permeable laminate 20 is bonded to the bottom surface of the chip base to enclose the channels 16 as shown in FIGS. 2 and 11. Typically the laminate 20 is bonded to the chip base 12 by heat lamination, solvent bonding, adhesion (with wet or dry adhesives), or by other means depending on the specific materials used for the chip base 12 and laminate 20 respectively.

It is also possible to make the chip base 12 entirely out of the gas permeable polymer. Doing so may have advantages in providing a simpler lamination process, since both the laminate 20 and chip base 12 would then have identical material properties. However there may not be a significant gain in oxygen availability because the oxygen has to diffuse across a thick chip base (in the order of millimeters) versus a thin laminate (in the order of tens to hundreds of micrometers). The specialised gas permeable plastics may also have material properties that make them unsuitable for injection molding. For these reasons, in the preferred embodiment the chip base 12 is fabricated out of standard injection moldable plastics and the device is laminated with a thin gas permeable laminate.

The microfluidic platform or chip 10 of the present invention is capable of replicating the in vivo behavior of cells in a culture system. Applications of the microfluidic platform or chip 10 may include (but are not limited to):

Research tools for academic and industrial RandD

Drug discovery tools for pharmaceutical companies

Assistive tools for tailoring clinical therapies to individual patients

Ease of use is a critical differentiator for the academic RandD customer segment. Besides the inconvenience of PDMS chip fabrication, users face other usage difficulties including:

Daily changing of media—Microfluidic devices have small culture media volumes within each channel (typically tens of microliters). This means that the nutrient content of the medium will be exhausted quickly by the cultured cells, and the medium must be changed daily. Since users have to change media for many small devices, the process needs to be simple, rapid and error-proof. Culture medium is typically aspirated out of the microfluidic channels with a pipette tip attached to vacuum suction. A common error that occurs is over-aspiration where too much vacuum force is applied, resulting in cells being sucked out of the channels along with the culture medium, resulting in cell loss/death.

Flexibility: Researchers value the flexibility to experiment with different setups, e.g. by connecting other devices and equipment to the culture system to modify the culture conditions. Current users have to fashion their own connections, which may be inconvenient and unreliable.

Handling: Users want microfluidic chips that make optimal use of the limited space in their incubators. The chips also need to be transported to tissue culture hoods and to various microscope platforms without spillage or contamination. Automated handling of devices (by robotic platforms, for example) is limited to certain form factors like microtiter plates.

Evaporation control—Microfluidic devices have small culture media volumes, so evaporation loss will cause significant changes in media osmolarity, resulting in unfavourable culture conditions. Users have to set up humidity chambers inside incubators to combat evaporation.

A number of innovations have been incorporated into the preferred embodiment of the microfluidic platform or chip 10 to overcome the usage difficulties outlined above. These additional innovations will now be described in detail.

A. Rapid Changing of Media Without Over-Aspiration

Figure 3:
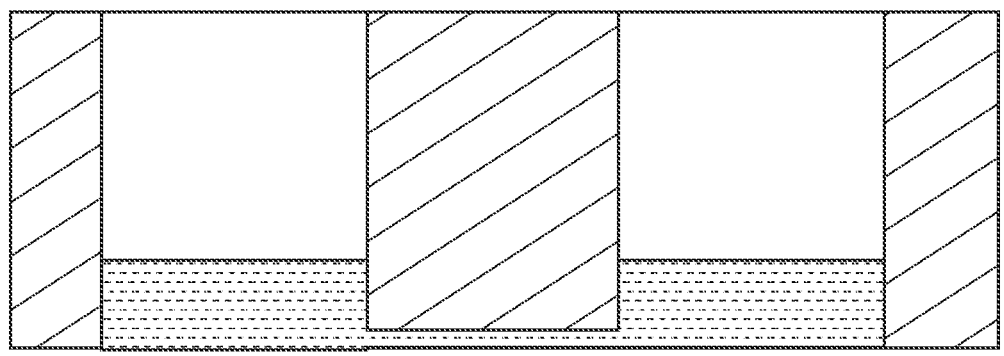
FIG. 3 is a cross-sectional view of a prior art microfluidic platform showing a configuration of conventional ports.

Prior art microfluidic port designs are cylindrical in shape, leading directly into the channels (see FIG. 3). Vacuum suction during the changing of culture medium can lead to cells being sucked out of the channels. An improved port design involves making internal troughs that are deeper than internal inlets (see FIG. 4). Each port 14 has an internal inlet 22, connecting the port 14 with the microfluidic channel 16, and a trough 24 for containing a small reservoir of culture medium fluid adjacent to the inlet 22 wherein, in use, culture medium can be aspirated from the microfluidic channel 16 via the trough 24 rather than directly via the internal inlet 22.

Figure 4:
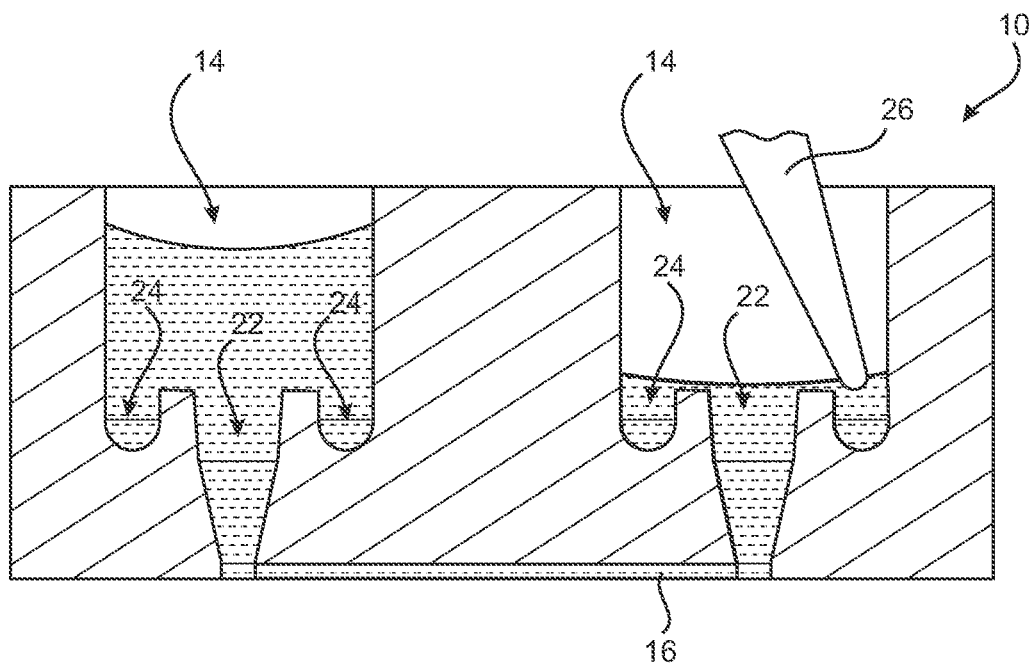
FIG. 4 is a cross-sectional view of a microfluidic platform according to the present invention showing a preferred configuration of improved ports.

In the illustrated embodiment the inlet 22 is provided centrally of the port 14 and the trough 24 is of annular configuration surrounding the inlet in a concentric circle (as shown in cross-section in FIG. 4). Alternatively, the trough 24 may be of a different configuration yet still placed adjacent to the inlet 22. Typically the bottom of the trough is of semicircular cross-section.

The application of a vacuum through a glass/pipette tip 26 placed in the trough 24, as shown in FIG. 4, results in the removal of culture medium fluid, stopping when the medium in the trough is completely removed. Due to the higher height of the internal inlet 22, the culture medium and cells in the channel would not be affected by the vacuum aspiration, no matter how long the pipette tip is kept in the trough 24. Fresh medium can then be added to the port on one side of the channel 16 (the 'upstream' port), and allowed to flow through the channel, replacing the old medium. As a consequence of surface tension effects in microfluidic systems, a small volume of fresh media may need to be added to the downstream port, so that surface tension at the downstream inlet can be overcome to allow incoming flow.

B. Flexibility Through Modular Luer Connectors and Interfaces

Figure 5:
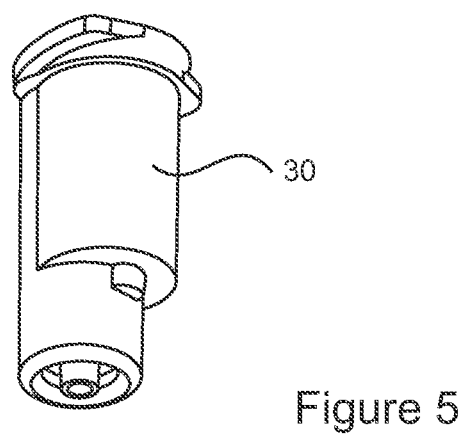
FIG. 5 illustrates a preferred modular luer connector that can be employed with a microfluidic platform according to the present invention.
Figure 6:
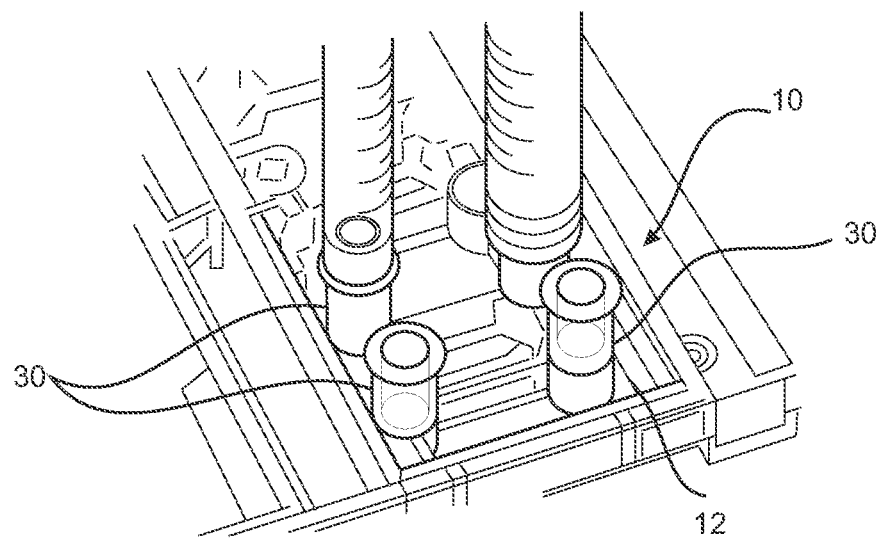
FIG. 6 illustrates modular luer connectors connected to the ports in a microfluidic platform according to the present invention.

The chip channel ports 14 are preferably designed as modular attachment interfaces. AIM's universal luer lock connector 30 (as shown in FIG. 5) enables users to attach standard luer fittings (e.g. for attaching tubing connectors and syringe pumps) to the microfluidic chip 10. Future accessories developed by AIM may connect directly to the ports 14 or via the universal connectors. FIG. 5 shows a plurality of the modular connectors 30 connected to respective ports 14 of the microfluidic platform 10. FIG. 5 shows both a connector for luer slip and luer lock connections (left), and connectors attached to luer slip and luer lock syringes (right).

Prior art approaches by other manufacturers are based on separate components built directly onto the chip. The connector components protrude out of the chip and are included in the chip by default. This present modular design has two important advantages:

(i) The microfluidic chips 10 can be made more efficiently out of a single material into a single component—Not all users want to connect to other devices. These users will have the option to use the basic chip 10 on its own. Other users that require connections to other devices have a separate option to use modular luer connectors. This design approach makes more economic sense to both the manufacturer and users, because the core platform (i.e. the chip) would be easier to manufacture, while the user community will get a lower price base and yet have more choices.

(ii) The ports play dual roles—The ports act as reservoirs that enable rapid media changing for users that do not require connections. Other users that need to connect to syringe pumps, etc. would use the ports as connecting interfaces. Note that the latter group of users would exchange media by using the connected devices such as pumps, so there is no need for the rapid media changing function. This approach optimises the use of the limited real estate on the chip. It also enables future accessories to be attached directly onto the chip itself with an interface that matches the port's trough and inlet, doing away with the extra component that other manufacturers use today.

C. Improving Handling with SBS/ANSI-Compliant Microplate Holders

Figure 7:
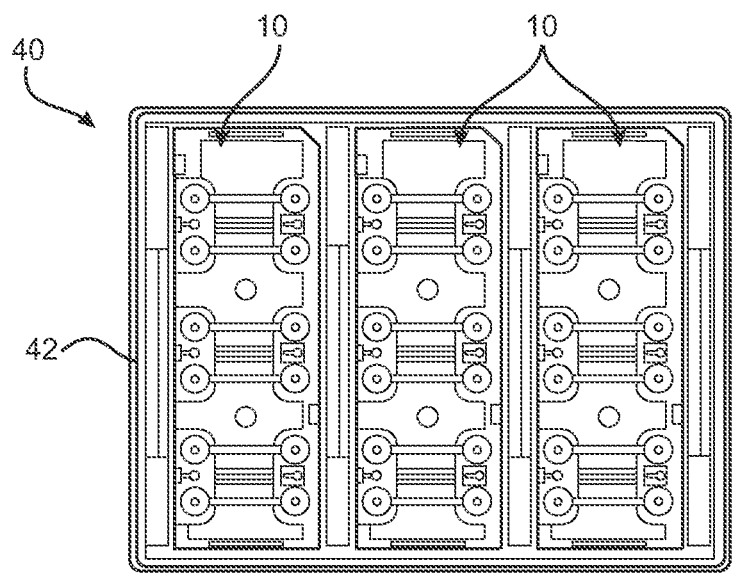
FIG. 7 is a plan view of one embodiment of a microplate holder for holding up to three microfluidic platforms according to the present invention.
Figure 9:
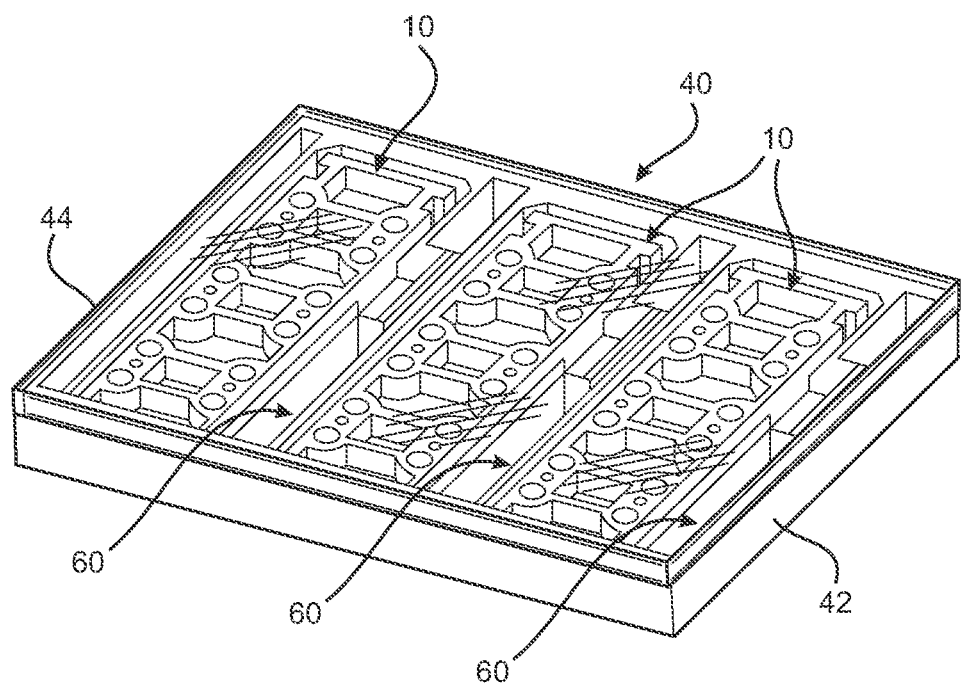
FIG. 9 illustrates the location of internal reservoirs provided in the microplate holder of FIG. 7.

Advantageously a plurality of the microfluidic chips 10 can be received and held in a single microplate holder 40, as shown in FIGS. 7 and 9. The illustrated embodiment of the microplate holder 40 comprises a tray 42, having side walls and a substantially planar base, and a plurality of compartments 46 provided in connection therewith. Each compartment 46 in the tray 42 is adapted to receive a microfluidic chip 10 therein. In the illustrated embodiment the tray 42 is designed to receive up to three of the fluidic chips 10 therein. Preferably the holder 40 further comprises a cover 44 which is received on top of the tray to enclose the microfluidic chips 10 therein. Advantageously the cover 44 is substantially transparent. Advantageously a plurality of the holders 40 is also stackable.

Standard form factors such as microscope slides and microtiter plates are prevalent in the biological and pharmaceutical research industries. Both the chips and holders are designed to comply with these existing standards so that the devices fit into existing workflows. The holders will also fit onto standard microscopy platforms and are stackable to maximise working space in cell culture incubators. The holders are designed to position the chip channel ports 14 to comply with SBS/ANSI standards for microtiter plates, so that they will be compatible with automated plate filling/handling systems. Such systems are made to fill wells in microplates and require the fill positions to be accurately located. A further advantage of this design approach is that devices suitable for manual operation in academic laboratories can also be deployed in an industrial, automated setting.

D. Humidity Control Through Chip and Holder Designs

Users of microfluidic systems often have to place their devices in humidity chambers to limit evaporation. Advantageously both the chips 10 and holders 40 have built-in reservoirs (see FIGS. 8 and 9) that can be filled with sterile water, hydrogels (e.g. agarose, polyacrylamide, etc.) or other substances to create a humid environment around the device (and within the holder). This approach does away with the need to set up a separate humidity chamber. It also facilitates easy handling and retention of humid conditions when transferring the devices onto imaging platforms, since the humidification function is built into the chips and holders themselves.

Figure 8:
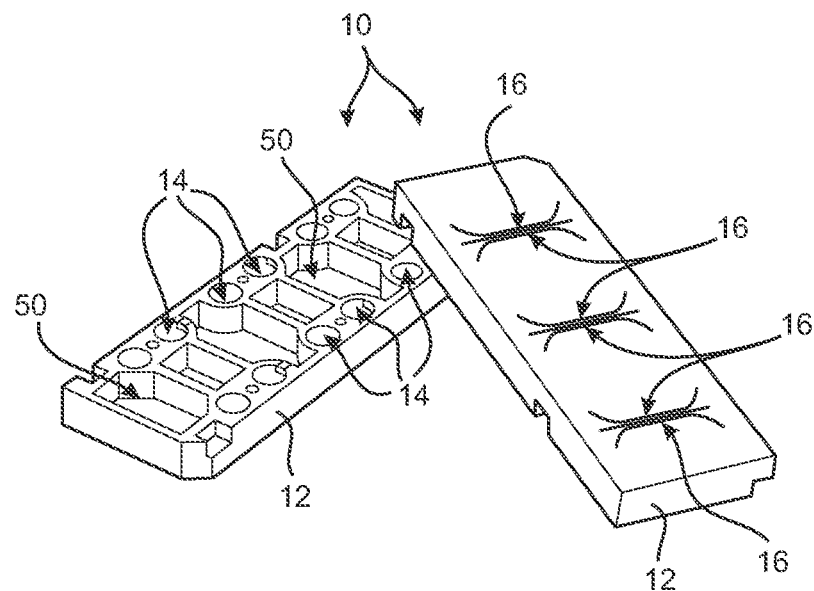
FIG. 8 is an isometric view of both the topside and underside of the microfluidic platform of FIG. 1, illustrating the location of internal reservoirs provided therein.

As can be seen most clearly in FIG. 8, the chip base 12 is formed with a plurality of reservoirs 50 molded into an upper surface thereof. The reservoirs 50 are not in fluid communication with the ports 14. In use, each reservoir can be used to hold sterile water, a hydrogel or other substance to create a humid environment around the device.

Likewise the holder 40 further comprises a plurality of internal reservoirs 60 provided within the tray 42, as can be seen most clearly in FIG. 9. The reservoirs 60 are separate from and not in fluid communication with the chips 10. Hence, in use, each reservoir 60 can be used to hold sterile water, a hydrogel or other substance to create a humid environment around the chips 10.

Now that preferred embodiments of the microfluidic platform have been described in detail, it will be apparent that it provides a number of advantages over the prior art, including the following:

(i) It overcomes the problems associated with using PDMS for the substrate of the chip;

(ii) Improved chip channel port design obviates the problems associated with over-aspiration;

(iii) The chip can be used on its own, or in conjunction with other devices using modular luer connectors;

(iv) Both chips and holders comply with SBS/ANSI standards for microtiter plates, so they are compatible with automated plate filling/handling systems; and, (v) Built-in reservoirs allow both the chips and holders to provide on-board humidity control.

It will be readily apparent to persons skilled in the relevant arts that various modifications and improvements may be made to the foregoing embodiments, in addition to those already described, without departing from the basic inventive concepts of the present invention. For example, the fluidic platforms or chips in the described embodiments are each provided with three sets of microfluidic channels. However the chips can be custom-designed to incorporate any desired number of channels and in a variety of configurations. Therefore, it will be appreciated that the scope of the invention is not limited to the specific embodiments described.

What is claimed is:

1. A microfluidic platform for investigating cell-based interactions, the platform comprising:
a chip base comprising a plurality of ports in fluid communication with a microfluidic channel for containing a fluid culture medium in which cells are held, each port comprising:
an internal inlet, connecting the port with the microfluidic channel,
a trough for containing a small reservoir of culture medium fluid adjacent to the inlet, and
an upper reservoir above said trough and said internal inlet,
wherein, in use, the fluid culture medium can be aspirated from the microfluidic channel via the trough rather than directly via the internal inlet.

2. The microfluidic platform as defined in claim 1, wherein the inlet is provided centrally of the port and the trough is of annular configuration surrounding the inlet.

3. The microfluidic platform as defined in claim 2, wherein the bottom of the trough is of semicircular cross-section.

4. The microfluidic platform as defined in claim 1, wherein the ports of the microfluidic platform are designed as interfaces for modular attachments.

5. The microfluidic platform as defined in claim 4, wherein the ports are adapted to receive a modular luer connector as a modular attachment for attaching standard luer fittings to the microfluidic platform.

6. The microfluidic platform as defined in claim 1, wherein the microfluidic platform is configured such that a plurality of the microfluidic platform can be received and held in a single microplate holder.

7. The microfluidic platform as defined in claim 6, wherein the holder further comprises a plurality of internal reservoirs, which are not in fluid communication with the chips, wherein, in use, each reservoir is adapted to hold sterile water, a hydrogel or other substance to create a humid environment around the chips.

8. The microfluidic platform as defined in claim 5, wherein the standard luer fittings are selected from the group consisting of tubing connectors, and syringe pumps.

9. A microfluidic platform for investigating cell-based interactions according to claim 1, wherein the chip base is made of a suitable plastics material with appropriate optical properties.

10. The microfluidic platform as defined in claim 9, wherein the chip base is made from an engineering plastics material that can be injection molded and is optically clear.

11. The microfluidic platform as defined in claim 10, wherein the plastics material is selected from the group consisting of polycarbonates (PC), polystyrenes (PS), polyethylenes (PE), cyclic olefin co-polymers (COC), and cyclic olefin polymers (COP).

12. The microfluidic platform as defined in claim 9, further comprising a gas permeable laminate bonded to a bottom surface of the chip base.

13. The microfluidic platform as defined in claim 12, wherein the gas permeable laminate is made from a polymer with low bulk density.

14. The microfluidic platform as defined in claim 13, wherein the polymer of low bulk density is selected from the group consisting of polymethylpentene (PMP), poly(1-trimethylsilyl-1-propyne) (PTMSP), polymethylated polymers, polymethylated poly(diphenylacetylene), and polymers that achieve sufficient gas permeability through other means.

15. The microfluidic platform as defined in claim 12, wherein the gas permeable laminate is optically clear.

16. The microfluidic platform as defined in claim 15, wherein the laminate is bonded to the chip base by heat lamination, solvent bonding, adhesion (with wet or dry adhesives), or by other means depending on the specific materials used for the chip base and laminate respectively.

17. The microfluidic platform as defined in claim 9, wherein the chip base has a plurality of microfluidic channels of elongate configuration arranged in a linear array, each microfluidic channel being substantially parallel to an adjacent channel.

18. The microfluidic platform as defined in claim 17, wherein each microfluidic channel has a pair of ports, one port provided at each end respectively.

19. The microfluidic platform as defined in claim 18, wherein the ports all open onto an upper surface of the chip base.

20. The microfluidic platform as defined in claim 18, wherein the microfluidic channels are arranged into pairs with a third microfluidic channel provided there between, the third channel being configured so as to permit controlled fluid communication between the pair of microfluidic channels and the third microfluidic channel.

21. The microfluidic platform as defined in claim 20, wherein the third microfluidic channel is filled with a hydrogel or other extracellular matrix.

22. The microfluidic platform as defined in claim 21, wherein all of the microfluidic channels are formed in a bottom surface of the chip base and a gas permeable laminate is bonded to the bottom surface of the chip base to enclose the channels.

23. The microfluidic platform as defined in claim 18, wherein the chip base is formed with a plurality of reservoirs molded into the upper surface thereof which are not in fluid communication with the ports, wherein, in use, each reservoir is adapted to hold sterile water, a hydrogel or other substance to create a humid environment around the device.

24. The microfluidic platform as defined in claim 9, wherein the chip base is of generally elongate, rectangular configuration, with the ports arranged along its respective longitudinal edges.

25. A method of manufacturing a microfluidic platform for investigating cell-based interactions according to claim 9, the method comprising:
molding the chip base from the suitable plastics material so as to include the plurality of ports.

26. The method of manufacturing a microfluidic platform as defined in claim 25, wherein the step of molding the chip base comprises injection molding using an engineering plastics material that is optically clear.

27. The method of manufacturing a microfluidic platform as defined in claim 26, wherein the plastics material is selected from the group consisting of polycarbonates (PC), polystyrenes (PS), polyethylenes (PE), cyclic olefin co-polymers (COC), and cyclic olefin polymers (COP).

28. The method of manufacturing a microfluidic platform as defined in claim 25, wherein the method further comprises the step of bonding a gas permeable laminate to a bottom surface of the chip base.

29. The method of manufacturing a microfluidic platform as defined in claim 28, wherein the gas permeable laminate is optically clear and is made from a polymer with low bulk density.

30. The method of manufacturing a microfluidic platform as defined in claim 29, wherein the polymer of low bulk density is selected from the group consisting of polymethylpentene (PMP), poly(1-trimethylsilyl-1-propyne) (PTMSP), polymethylated polymers, polymethylated poly(diphenylacetylene), and polymers that achieve sufficient gas permeability through other means.

31. The method of manufacturing a microfluidic platform as defined in claim 28, wherein the step of bonding the laminate to the chip base comprises laminating the laminate to the chip base by heat lamination.

32. The method of manufacturing a microfluidic platform as defined in claim 28, wherein the step of bonding the laminate to the chip base comprises solvent bonding, adhesion bonding (with wet or dry adhesives), or other bonding means depending on the specific materials used for the chip base and laminate respectively.

* * * * *